US009006227B2

(12) United States Patent
Sonesson et al.

(10) Patent No.: US 9,006,227 B2
(45) Date of Patent: Apr. 14, 2015

(54) MODULATORS OF CORTICAL DOPAMINERGIC- AND NMDA-RECEPTOR-MEDIATED GLUTAMATERGIC NEUROTRANSMISSION

(75) Inventors: Clas Sonesson, Billdal (SE); Jonas Karlsson, Göteborg (SE); Peder Svensson, Göteborg (SE)

(73) Assignee: Integrative Research Laboratories Sweden AB, Göteborg (SE)

( * ) Notice: Subject to any disclaimer, the term of this patent is extended or adjusted under 35 U.S.C. 154(b) by 0 days.

(21) Appl. No.: 14/112,080

(22) PCT Filed: Apr. 17, 2012

(86) PCT No.: PCT/EP2012/056959
§ 371 (c)(1),
(2), (4) Date: Oct. 16, 2013

(87) PCT Pub. No.: WO2012/143337
PCT Pub. Date: Oct. 26, 2012

(65) Prior Publication Data
US 2014/0128360 A1 May 8, 2014

Related U.S. Application Data

(60) Provisional application No. 61/476,810, filed on Apr. 19, 2011.

(30) Foreign Application Priority Data

Apr. 19, 2011 (DK) .................................. 2011 70187
Sep. 6, 2011 (DK) .................................. 2011 70495

(51) Int. Cl.
| | |
|---|---|
| A61K 31/397 | (2006.01) |
| A61K 31/4453 | (2006.01) |
| C07D 205/04 | (2006.01) |
| C07D 211/22 | (2006.01) |
| C07C 317/22 | (2006.01) |
| C07D 295/088 | (2006.01) |

(52) U.S. Cl.
CPC ............ *C07C 317/22* (2013.01); *C07D 205/04* (2013.01); *C07D 295/088* (2013.01); *C07D 211/22* (2013.01); *C07B 2200/05* (2013.01); *C07C 2101/02* (2013.01); *C07C 2101/04* (2013.01); *C07C 2101/08* (2013.01)

(58) Field of Classification Search
None
See application file for complete search history.

(56) References Cited

U.S. PATENT DOCUMENTS 5,767,132 A 6/1998 Bottcher et al.

FOREIGN PATENT DOCUMENTS

| CN | 1130180 A | 9/1996 |
|---|---|---|
| EP | 0363782 A1 | 4/1990 |
| JP | 2006-193494 A | 7/2006 |
| WO | WO-02/00602 A1 | 1/2002 |
| WO | WO-2007/063789 A1 | 6/2007 |
| WO | WO-2007/072041 A1 | 6/2007 |
| WO | WO-2009/133107 A1 | 11/2009 |
| WO | WO-2009/133109 A1 | 11/2009 |
| WO | WO-2009/133110 A1 | 11/2009 |

OTHER PUBLICATIONS

Pubmed printout of "Lawrence et al. The D1 receptor antagonist, SCH23390, induces signs of Parkinsonism in African green monkeys. Life Science, 1991, 49, PL229-234".*
Chen et al., Design, Synthesis, and Evaluation of Potent and Selective Ligands for the Dopamine 3 (D3) Receptor with a Novel in Vivo Behavioral Profile. Journal of Medicinal Chemistry, 2008, 51, 5905-5908.*
Pubmed printout of "Kramer et al., The effects of a selective D4 dopamine receptor antagonist (L-745, 870) in acutely psychotic inpatients with schizophrenia. D4 Dopamine Antagonist Group. Archives of General Psychiatry, 1997, 54, 567-572".*
Pubmed printout of "Kilic et al., Effects of dehydroepianodrosterone in amphetamine-induced schizophrenia models in mice. Neuroscience. 2014, 19, 100-105".*
Shafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
CAPLUS printout of Japanese Patent No. 51123821.*
Alexander GE, et al. (1986) Parallel Organization of Functionally Segregated Circuits Linking Basal Ganglia and Cortex. *Ann. Rev. Neurosci.*, 9: 357-381.
Bramham CR, et al. (2010) The Arc of synaptic memory. *Exp. Brain Res.*, 200: 125-140.
Cepeda C, et al. (2010) Genetic mouse models of Huntington's disease: focus on electrophysiological mechanisms. *ASN Neuro*, 2(2): e00033.
Chomczynski P, et al. (1987) Single-step method of RNA isolation by acid guanidinium thiocyanate-phenol-chloroform extraction. *Anal. Biochem.*, 162: 156-159.
Crespi CL, et al. (2000) Fluorometric screening for metabolism based drug-drug interactions. *J. Pharm. Tox. Meth.*, 44: 325-331.
Forlin L, et al. (1980) Effects of clophen A50, 3-methylcholanthrene, pregnenolone-16 alpha-carbonitrile, and phenobarbital on the hepatic microsomal cytochrome P-450-dependent monooxygenase system in rainbow trout, *Salmo gairdneri*, of different age and sex. *Tox Appl Pharm.*, 54(3): 420-430.

(Continued)

*Primary Examiner* — Michael Barker
*Assistant Examiner* — Po-Chih Chen
(74) *Attorney, Agent, or Firm* — Ballard Spahr LLP

(57) ABSTRACT

The present invention relates to novel substituted phenoxyethylamine derivatives, useful as modulators of cortical and basal ganglia dopaminergic and N-methyl-D-aspartate (NMDA) receptor-mediated glutamatergic neurotransmission. In other aspects the invention relates to the use of these compounds in a method for therapy and to pharmaceutical compositions comprising the compounds of the invention.

17 Claims, No Drawings

(56) References Cited

OTHER PUBLICATIONS

Kawashima T, et al. (2009) Synaptic activity-responsive element in the *Arcl Arg3.1* promoter essential for synapse-to-nucleus signaling in activated neurons. *PNAS*, 106(1): 316-321.

Link W, et al. (1995) Somatodendritic expression of an immediate early gene is regulated by synaptic activity. *Proc Natl Acad Sci USA*, 92: 5734-5738.

Lyford GL, et al. (1995) Arc, a Growth Factor and Activity-Regulated Gene, Encodes a Novel Cytoskeleton-Associated Protein That Is Enriched in Neuronal Dendrites. *Neuron*, 14: 433-445.

Moghaddam B, et al. (1989) Ionic composition of microdialysis perfusing solution alters the pharmacological responsiveness and basal outflow of striatal dopomine. *J. Neurochem.*, 53: 652-654.

Paxinos G, et al. (1986) The Rat Brain in Stereotaxic Coordinates. NY, Academic Press.

Psychopharmacology 4th Generation of progress, Chapter 68, p. 793-795, (1995).

Psychopharmacology 4th Generation of progress, Chapter 101, p. 1205 and 1207,(1995).

Psychopharmacology 4th Generation of progress, Chapter 101, p. 1208-1209, (1995).

Raubo P, et al. (2006) Aminoalkyl phenyl sufones—a novel series of 5-HT7 receptor ligands. *Bioorganic & Medicinal Chemistry Letters, Pergamon, Elsevier Science*, GB, 16(5); 1255-1258.

Renwick AB, et al. (2001) Metabolism of 2,5-bis(trifluoromethyl)-7-benzyloxy-4-trifluoromethylcoumarin by human hepatic CYP isoforms: evidence for selectivity towards CYP3A4. *Xenobiotica*, 31(4): 187-204.

Santiago M, et al. (1990) Characterization of the in vivo release of dopamine as recorded by different types of intracerebral microdialysis probes. *Naunyn-Schmiedeberg's Arch. Pharmacol.*, 342: 407-414.

Steward O, et al. (2001) Selective targetting of newly synthesised Arc mRNA to active synapses requires NMDA receptor activation. *Neuron*, 30: 227-240.

Waters, et al. (1994) Differential effects of dopamine D2 and D3 receptor antagonists in regard to dopamine release, in vivo receptor displacement and behaviour. *J. Neural. Transm. Gen. Sect.I* 98(1): 39-55.

International Preliminary Report on Patentability issued by the International Bureau on Oct. 22, 2013 for International Application No. PCT/EP2012/056959 filed Apr. 19, 2011 and published as WO 2012/143337 on Oct. 26, 2012 (Applicants—Integrative Research Laboratories Sweden AB; Inventors—Sonesson, et al.) (5 pages).

International Search Report mailed by the International Bureau on Sep. 20, 2012 for International Application No. PCT/EP2012/056959 filed Apr. 19, 2011 and published as WO 2012/143337 on Oct. 26, 2012 (Applicants—Integrative Research Laboratories Sweden AB; Inventors—Sonesson, et al.) (4 pages).

Written Opinion mailed by the International Bureau on Sep. 20, 2012 for International Application No. PCT/EP2012/056959 filed Apr. 19, 2011 and published as WO 2012/143337 on Oct. 26, 2012 (Applicants—Integrative Research Laboratories Sweden AB; Inventors—Sonesson, et al.) (4 pages).

Jaques J, et al. (1981) Enantiomers, Racemates and Resolutions. Section 5: Formation and Separation of Diastereomers. pp. 251-368. John Wiley and Songs, New York.

King RE. Remington's Pharmaceutical Sciences. Part 8: Pharmaceutical Preparations and Their Manufacture, pp. 1409-1662. Maack Publishing Co., Easton PA. (1975).

Stahl PH, et al. (2002) Handbook of Pharmaceutical Salts: Properties, Selection, and Use. Wiley-VCH. pp. 1-372.

\* cited by examiner

MODULATORS OF CORTICAL DOPAMINERGIC- AND NMDA-RECEPTOR-MEDIATED GLUTAMATERGIC NEUROTRANSMISSION

CROSS-REFERENCE TO RELATED APPLICATIONS

The present application is a U.S. National Phase Application of International Application No. PCT/EP2012/056959, filed Apr. 17, 2012, which claims priority to Danish Patent Application No. PA 2011 70187, filed Apr. 19, 2011; U.S. Provisional Patent Application No. 61/476,810, filed Apr. 19, 2011; and Danish Patent Application No. PA 2011 70495, filed Sep. 6, 2011, all of which applications are incorporated herein fully by this reference.

REFERENCE TO SEQUENCE LISTING

The Sequence Listing submitted Dec. 3, 2013 as a text file named "37441_0001U1_Sequence_Listing.txt," created on Nov. 20, 2013, and having a size of 1,781 bytes is hereby incorporated by reference pursuant to 37 C.F.R. §1.52(e)(5).

TECHNICAL FIELD

The present invention relates to novel substituted phenoxy-ethyl-amine derivatives, useful as modulators of cortical and basal ganglia dopaminergic and N-methyl-D-aspartate (NMDA) receptor-mediated glutamatergic neurotransmission. In other aspects the invention relates to the use of these compounds in a method for therapy and to pharmaceutical compositions comprising the compounds of the invention.

BACKGROUND ART

Dopamine is a neurotransmitter in the brain. Since this discovery, made in the 1950's, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly at central dopamine receptors are commonly used in the treatment of neurological and psychiatric disorders, e.g. Huntington and Parkinson's disease and schizophrenia.

Antipsychotic drugs (or neuroleptics) are a class of compounds with diverse effects on different receptor systems. However, they have in common the ability to block dopamine $D_2$ receptors in the basal ganglia (i.e. striatum) and are used to manage psychosis (including delusions or hallucinations, as well as disordered thought), particularly in schizophrenia and bipolar disorder.

The cerebral cortex encompasses several major regions that are involved in higher functions such as thought, feelings, memory and planning. Biogenic amines such as dopamine are important for mammalian cortical function. The ascending dopamine pathways innervate the cortex. Primary or secondary dysfunctions in the activity of these pathways lead to dysregulation of the activity at dopamine in these brain areas and subsequently to manifestations of psychiatric and neurological symptoms. Both dopamine $D_1$ and N-methyl-D-aspartate (NMDA) receptors in the prefrontal cortex play a critical role in synaptic plasticity, memory mechanisms, and cognition.

Huntington's disease (HD) is a rare neurodegenerative disorder of the central nervous system characterized by progressive deterioration of motor and cognitive functions as well as behavioural and psychiatric disturbances. It is well established that certain aspect of dopaminergic functions are also affected in Huntington's disease. Neuropathological changes in Huntington's disease involve prominent cell loss and atrophy in the striatum but also in many other brain regions such as the cortex, substantia nigra, hypothalamus, cerebellum and thalamus.

In HD, glutamate and dopamine (DA) transmission is altered, which is likely to induce an imbalance in activity of the direct and indirect pathways and to contribute to the motor, cognitive, and psychiatric symptoms of HD (i.e. communication between the cortex and striatum, Capeda et al; *ASN Neuro* 2010 2 (2) e00033). Therefore, compounds which can strengthen the cortical dopamine and NMDA transmission, and exert antagonism of excessive subcortical dopamine transmission, can balance aberrant functioning in the cortico-striato-thalamic network controlling motor functions (Alexander et al; *Ann. Rev. Neurosci.* 1986 9 357-381).

JP 2006-193494 (Dainippon Ink and Chemicals, Inc) describes certain quaternary ammonium compounds useful as therapeutic agent for heart diseases.

WO 2009/133107 (NSAB, Filial af NeuroSearch Sweden AB, Sverige) describes certain 1-(2,3-dihydro-1,4-benzodioxin-2-yl)methanamine derivatives, WO 2009/133109 (NSAB, Filial af NeuroSearch Sweden AB, Sverige) describes certain 1-(2,3-dihydro-1,4-benzodioxin-2-yl) methanamine derivatives, and WO 2009/133110 (NSAB, Filial af NeuroSearch Sweden AB, Sverige) describes certain 1-(4H-1,3-benzodioxin-2-yl)methanamine derivatives, useful as modulators of dopamine neurotransmission, and more specifically as dopaminergic stabilizers. However, the phenoxy-ethyl-amine derivatives of the present invention have not previously been reported.

SUMMARY OF THE INVENTION

The object of the present invention is to provide novel pharmaceutically active compounds, especially useful in treatment of disorders in the central nervous system. A further object is the provision of compounds for modulation of dopaminergic and glutamatergic systems in the mammalian brain, including human brain.

In its first aspect, the invention provides a phenoxy-ethyl-amine derivative of Formula 1

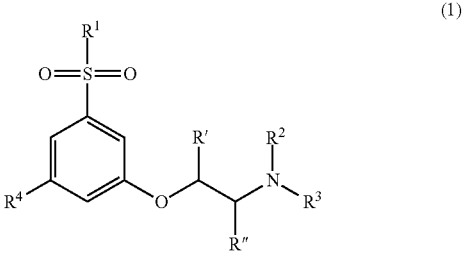

(1)

a stereoisomer or a mixture of its stereoisomers, or an N-oxide thereof, or a fully or partially deuterated analog thereof, or a pharmaceutically acceptable salt thereof, wherein $R^1$, $R^2$, $R^3$, $R^4$, R' and R" are as defined below.

In its second aspect, the invention provides a pharmaceutical composition, comprising a therapeutically effective amount of a phenoxy-ethyl-amine derivative of the invention, a stereoisomer or a mixture of its stereoisomers, or an N-oxide thereof, or a pharmaceutically acceptable salt thereof, together with at least one pharmaceutically acceptable carrier, excipient or diluent.

In a further aspect, the invention provides the use of a phenoxy-ethyl-amine derivative of the invention, a stereoisomer or a mixture of its stereoisomers or an N-oxide thereof, or a pharmaceutically acceptable salt thereof, for the manufacture of a pharmaceutical composition for the treatment, prevention or alleviation of a disease or a disorder or a condition of a mammal, including a human, which disease, disorder or condition is responsive to responsive to modulation of dopaminergic and glutamatergic function in the central nervous system.

In a still further aspect, the invention relates to a method for treatment, prevention or alleviation of a disease or a disorder or a condition of a living animal body, including a human, which disorder, disease or condition is responsive to modulation of dopaminergic and glutamatergic function in the central nervous system, which method comprises the step of administering to such a living animal body in need thereof a therapeutically effective amount of a phenoxy-ethyl-amine derivative of the invention, a stereoisomer or a mixture of its stereoisomers, or an N-oxide thereof, or a pharmaceutically acceptable salt thereof.

Other aspects of the invention will be apparent to the person skilled in the art from the following detailed description and examples.

DETAILED DESCRIPTION OF THE INVENTION

Phenoxyethylamine Derivatives

In its first aspect the present invention provides phenoxy-ethyl-amine derivatives of Formula 1

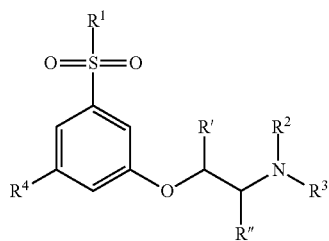

(1)

a stereoisomer or a mixture of its stereoisomers, or an N-oxide thereof, or a fully or partially deuterated analog thereof, or a pharmaceutically acceptable salt thereof, wherein $R^1$ represents $CH_3$ or $CF_3$;

$R^2$ is selected from the group consisting of $C_1$-$C_4$-alkyl, allyl, $CH_2CH_2OCH_3$, $C(CH_3)_2CH_2CH_3$, $CH_2$-cyclopropyl, cyclobutyl, cyclopentyl, $CH_2CH_2CH_2F$, $CH_2CH_2CHF_2$, $CH_2CH_2F$, 3,3,3-trifluoropropyl and 4,4,4-trifluorobutyl; and $R^3$ is selected from the group consisting of H, $CH_3$ and $CH_2CH_3$; or $R^2$ and $R^3$ together form $CH_2(CH_2)CH_2$ or $CH_2(CH_2)_3CH_2$;

$R^4$ represents F or Cl; and

R' and R" independently represent hydrogen or methyl.

In a preferred embodiment the phenoxy-ethyl-amine derivative of the invention is a compound of Formula 1a

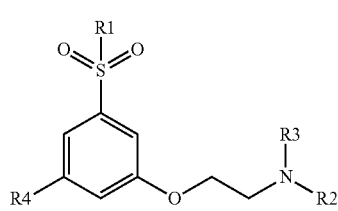

(1a)

a stereoisomer or a mixture of its stereoisomers, or an N-oxide thereof, or a pharmaceutically acceptable salt thereof, wherein $R^1$ is selected from the group consisting of $CH_3$ or $CF_3$;

$R^2$ is selected from the group consisting of $C_1$-$C_4$ alkyl, allyl, $CH_2CH_2OCH_3$, $C(CH_3)_2CH_2CH_3$, $CH_2$-cyclopropyl, $CH_2CH_2CH_2F$, $CH_2CH_2CHF_2$, $CH_2CH_2F$, 3,3,3-trifluoropropyl and 4,4,4-trifluorobutyl;

$R^3$ is selected from the group consisting of H, $CH_3$ and $CH_2CH_3$; and $R^4$ is selected from the group consisting of F and Cl.

In another preferred embodiment the phenoxy-ethyl-amine derivative of the invention is a compound of Formula 1a, a stereoisomer or a mixture of its stereoisomers, or an N-oxide thereof, or a pharmaceutically acceptable salt thereof, wherein $R^1$ is selected from the group consisting of $CH_3$ or $CF_3$;

$R^2$ is selected from the group consisting of $C_1$-$C_4$ alkyl, allyl, $CH_2CH_2OCH_3$, $C(CH_3)_2CH_2CH_3$, $CH_2$-cyclopropyl, cyclobutyl, cyclopentyl, $CH_2CH_2CH_2F$, $CH_2CH_2CHF_2$, $CH_2CH_2F$, 3,3,3-trifluoropropyl and 4,4,4-trifluorobutyl;

$R^3$ is selected from the group consisting of H, $CH_3$ and $CH_2CH_3$;

or $R^2$ and $R^3$ together form $CH_2(CH_2)_3CH_2$; and $R^4$ is selected from the group consisting of F and Cl.

In a third preferred embodiment the phenoxy-ethyl-amine derivative of the invention is a compound of Formula 1 or 1a, a stereoisomer or a mixture of its stereoisomers, or an N-oxide thereof, or a pharmaceutically acceptable salt thereof, wherein $R^1$ represents $CH_3$ or $CF_3$.

In a more preferred embodiment $R^1$ represents $CH_3$.

In another more preferred embodiment $R^1$ represents $CF_3$.

In a fourth preferred embodiment the phenoxy-ethyl-amine derivative of the invention is a compound of Formula 1 or 1a, a stereoisomer or a mixture of its stereoisomers, or an N-oxide thereof, or a pharmaceutically acceptable salt thereof, wherein $R^2$ is selected from the group consisting of $C_1$-$C_4$-alkyl, allyl, $CH_2CH_2OCH_3$, $C(CH_3)_2CH_2CH_3$, $CH_2$-cyclopropyl, cyclobutyl, cyclopentyl, $CH_2CH_2CH_2F$, $CH_2CH_2CHF_2$, $CH_2CH_2F$, 3,3,3-trifluoropropyl and 4,4,4-trifluorobutyl.

In a more preferred embodiment $R^2$ is selected from the group consisting of $C_1$-$C_4$-alkyl, $CH_2$-cyclopropyl, cyclobutyl and cyclopentyl.

In another more preferred embodiment $R^2$ represents $C_1$-$C_4$-alkyl.

In a third more preferred embodiment $R^2$ represents $CH_2$-cyclopropyl.

In a fourth more preferred embodiment $R^2$ represents cyclobutyl.

In a fifth more preferred embodiment $R^2$ represents cyclopentyl.

In a fifth preferred embodiment the phenoxy-ethyl-amine derivative of the invention is a compound of Formula 1 or 1a, a stereoisomer or a mixture of its stereoisomers, or an N-oxide thereof, or a pharmaceutically acceptable salt thereof, wherein $R^3$ is selected from the group consisting of H and $CH_3$.

In a more preferred embodiment $R^3$ represents H.

In another more preferred embodiment $R^3$ represents $CH_3$.

In a sixth preferred embodiment the phenoxy-ethyl-amine derivative of the invention is a compound of Formula 1 or 1a, a stereoisomer or a mixture of its stereoisomers, or an N-oxide thereof, or a pharmaceutically acceptable salt thereof, wherein $R^2$ and $R^3$ together form $CH_2(CH_2)CH_2$ or $CH_2(CH_2)_3CH_2$.

In a more preferred embodiment $R^2$ and $R^3$ together form $CH_2(CH_2)CH_2$.

In another more preferred embodiment $R^2$ and $R^3$ together form $CH_2(CH_2)_3CH_2$.

In a seventh preferred embodiment the phenoxy-ethyl-amine derivative of the invention is a compound of Formula 1 or 1a, a stereoisomer or a mixture of its stereoisomers, or an N-oxide thereof, or a pharmaceutically acceptable salt thereof, wherein $R^4$ represents F or Cl.

In a more preferred embodiment $R^4$ represents F.

In another more preferred embodiment $R^4$ represents Cl.

In an eight preferred embodiment the phenoxy-ethyl-amine derivative of the invention is a compound of Formula 1, a stereoisomer or a mixture of its stereoisomers, or an N-oxide thereof, or a pharmaceutically acceptable salt thereof, wherein R' and R" independently represent hydrogen or methyl.

In a more preferred embodiment one of R' and R" represents hydrogen; and the other of R' and R" represents methyl.

In another more preferred embodiment R' represents hydrogen; and R" represents methyl.

In a third more preferred embodiment R' represents methyl; and R" represents hydrogen.

In a fourth more preferred embodiment R' and R" both represents hydrogen.

In a fifth more preferred embodiment R' and R" both represents methyl.

In a most preferred embodiment the phenoxy-ethyl-amine derivative of the invention is N-[2-(3-Fluoro-5-methylsulfonyl-phenoxy)ethyl]propan-1-amine;

N-[2-(3-Fluoro-5-methylsulfonyl-phenoxy)ethyl]butan-1-amine;

N-ethyl-2-(3-fluoro-5-methylsulfonyl-phenoxy)ethanamine;

N-[2-(3-Fluoro-5-methylsulfonyl-phenoxy)ethyl]-N-methyl-propan-1-amine;

N-[2-(3-Chloro-5-methylsulfonyl-phenoxy)ethyl]propan-1-amine;

N-[2-(3-Fluoro-5-methylsulfonyl-phenoxy)ethyl]butan-2-amine;

N-[2-(3-Fluoro-5-methylsulfonyl-phenoxy)ethyl]cyclopentamine;

N-[2-(3-Fluoro-5-methylsulfonyl-phenoxy)ethyl]-2-methyl-butan-2-amine;

N-[2-(3-Fluoro-5-methylsulfonyl-phenoxy)ethyl]cyclobutamine;

N-[2-(3-Fluoro-5-methylsulfonyl-phenoxy)ethyl]propan-2-amine;

1-[2-(3-Fluoro-5-methylsulfonyl-phenoxy)ethyl]piperidine;

N,N-Diethyl-2-(3-fluoro-5-methylsulfonyl-phenoxy)ethanamine;

N-1,1-di-deuterium-propyl-[2-(3-fluoro-5-methanesulfonyl-phenoxy)-ethyl]-amine;

N-(Cyclopropylmethyl)-N-{2-[3-fluoro-5-(methylsulfonyl)-phenoxy]ethyl}amine;

N-{2-[3-Fluoro-5-(methylsulfonyl)phenoxy]ethyl}-N-isobutylamine;

1-[2-(3-Fluoro-5-methylsulfonyl-phenoxy)ethyl]azetidine;

1-(3-Fluoro-5-methylsulfonyl-phenoxy)-N-propyl-propan-2-amine; or 2-(3-Fluoro-5-methylsulfonyl-phenoxy)-N-propyl-propan-1-amine;

a stereoisomer or a mixture of its stereoisomers, or an N-oxide thereof, or a pharmaceutically acceptable salt thereof.

Any combination of two or more of the embodiments as described above is considered within the scope of the present invention.

DEFINITION OF TERMS

In the context of this invention $C_1$-$C_4$-alkyl means a straight chain or branched chain of one to four carbon atoms, including but not limited to, methyl, ethyl, n-propyl, i-propyl, n-butyl, i-butyl, s-butyl, t-butyl.

The term "allyl" refers to the group $—CH_2—CH=CH_2$.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

Pharmaceutically Acceptable Salts

The compound of the invention may be provided in any form suitable for the intended administration. Suitable forms include pharmaceutically (i.e. physiologically) acceptable salts of the compound of the invention.

Such pharmaceutically acceptable salts and common methodology for preparing them are known in the art. Further details may be found in P Stahl et al, Handbook of Pharmaceutical Salts: Properties, Selection and Use; Wiley-VCH, 2002.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may exist in different stereoisomeric forms, including enantiomers, diastereomers or cis-trans-isomers.

The invention includes all such isomers and any mixtures thereof including racemic mixtures.

Racemic forms can be resolved into the optical antipodes by known methods and techniques. One way of separating the enantiomeric compounds (including enantiomeric intermediates) is, in the case the compound being a chiral acid, by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates, or camphorsulphonate) salts for example.

The chemical compounds of the present invention may also be resolved by the formation of diastereomeric amides by reaction of the chemical compounds of the present invention with an optically active carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

N-Oxides

In the context of this invention an N-oxide designates an oxide derivative of a tertiary amine, including a nitrogen atom of an aromatic N-heterocyclic compound, a non-aromatic N-heterocyclic compounds, a trialkylamine and a trialkenylamine.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{11}$C, $^{13}$C, $^{14}$C, $^{131}$I, $^{125}$I, $^{123}$I and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Deuterated Analogs

The compounds of the invention may be provided in the form of their deuterated analogs. Deuterium forms bonds with carbon that vibrate at a lower frequency and are thus stronger than C—H bonds. Therefore "heavy hydrogen" (deuterium) versions of drugs may be more stable towards degradation and last longer in the living organism.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Persons skilled in the art will appreciate that, in order to obtain compounds of the invention in an alternative, and in some occasions, more convenient manner, the individual process steps mentioned hereinbefore may be performed in a different order, and/or the individual reactions may be performed at different stage in the overall route (i.e. chemical transformations may be performed upon different intermediates to those associated hereinbefore with a particular reaction).

Biological Activity

The compounds according to the present invention possess modulation of cortical and basal ganglia dopaminergic and N-methyl-D-aspartate (NMDA) receptor-mediated glutamatergic neurotransmission and both they and their pharmaceutical compositions are useful in treating numerous central nervous system disorders, including both psychiatric and neurological disorders. Particularly, the compounds and their pharmaceutical compositions may be used in the treatment of CNS disorders where the dopaminergic and glutamatergic system is dysfunctional due to direct or indirect causes.

The compounds and compositions according to the invention can be used to improve all forms of psychosis, including schizophrenia and schizophreniform and bipolar disorders as well as drug induced psychotic disorders. Iatrogenic psychoses and hallucinoses and non-iatrogenic psychoses and hallucinoses may also be treated.

In a special embodiment the disease, disorder or condition contemplated according to the invention is a form of psychosis, in particular schizophrenia, a schizophreniform disorder, a bipolar disorder, or a drug induced psychotic disorder.

Mood and anxiety disorders, depression and obsessive-compulsive disease may also be treated with the compounds and compositions according to the invention.

Compounds with modulating effects on dopaminergic and glutamatergic systems may also be used to improve motor and cognitive functions and in the treatment of emotional disturbances related to ageing, neurodegenerative (e.g.

dementia and age-related cognitive impairment) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds and environmental toxins The compounds and pharmaceutical compositions according to the invention may also be used in behavioural disorders usually first diagnosed in infancy, childhood, or adolescence as well as in impulse control disorders.

They can also be used for treating substance abuse disorders as well as disorders characterized by misuse of food. They are further useful for treatment of a condition selected from the group consisting of sleep disorders, sexual disorders, eating disorders, obesitas, and headaches and other pains in conditions characterized by increased muscular tone.

Neurological indications include the use of the compounds and their pharmaceutical compositions to improve mental and motor function in Parkinson's disease, and in related parkinsonian syndromes, dyskinesias (including L-DOPA induced dyskinesias and tardive dyskinesias) and dystonias. They may also be used to ameliorate tics and tremor of different origins.

They can also be used in the treatment of Huntington's disease and other movement disorders as well as movement disorders induced by drugs. Restless legs and related disorders as well as narcolepsy may also be treated with compounds included according to the invention.

The compounds and their pharmaceutical compositions according to the present invention can be used for the treatment of Alzheimer's disease or related dementia disorders.

In a further embodiment the disease, disorder or condition contemplated according to the invention is selected from the group of schizophrenia, L-DOPA induced dyskinesias and Huntington's disease.

Pharmaceutical Compositions

In another aspect the invention provides novel pharmaceutical compositions comprising a therapeutically effective amount of a compound of the invention.

While a compound of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, cellulose, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tra-gacanth; pastilles comprising the active ingredient in an inert base such as gelatin and glycerine or sucrose and acacia; and mouth-washes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including in-tranasal compositions, the compound will generally have a small particle size for example of the order of 5 microns or less. Such a particle size may be obtained by means known in the art, for example by micronization.

When desired, compositions adapted to give sustained release of the active in-gredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

In one embodiment, when the pharmaceutical composition of the invention is intended for treating patients with abuse liability and withdrawal symptoms caused by nicotine addiction, formulations such as gums, patches, sprays, inhalers, aerosols, etc. are contemplated.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, the exact mode of administration and form of administration, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

The compounds of the present invention are modulators of cortical and basal ganglia dopaminergic and N-methyl-D-aspartate (NMDA) receptor-mediated glutamatergic neurotransmission and therefore useful for the treatment of a range of ailments involving modulation of dopaminergic and glutamatergic function.

In another aspect the invention provides a method for the treatment, prevention or alleviation of a disease or a disorder or a condition of a living animal body, including a human, which disease, disorder or condition is responsive to modulation of dopaminergic and glutamatergic function in the central nervous system, and which method comprises administering to such a living animal body, including a human, in need thereof an effective amount of a compound of the invention, a stereoisomer or a mixture of its stereoisomers, or a pharmaceutically acceptable salt thereof.

The indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated in the examples below and as outlined below in Scheme 1, which in no way are intended to limit the scope of the invention.

Scheme 1

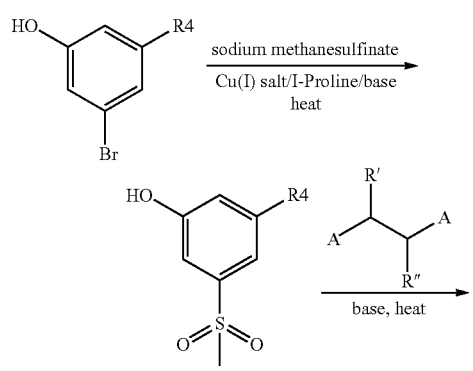

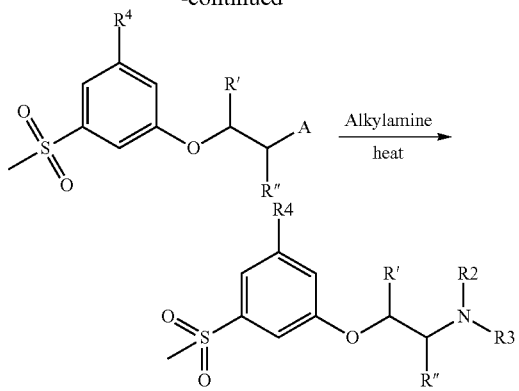

The substituents in Scheme 1 are as follows: A is a leaving group, and $R^2$, $R^3$, $R^4$, R' and R" are as defined above.

Example 1

N-[2-(3-FLUORO-5-METHYLSULFONYL-PHENOXY)ETHYL]PROPAN-1-AMINE

A mixture of 1-(2-bromoethoxy)-3-fluoro-5-methylsulfonyl-benzene (2.65 g, 8.9 mmol) and propan-1-amine (5.24 ml, 63.7 mmol) in ethanol (32 ml) was divided into 3 aliquots which were each heated under microwave radiation at 120° C. for 30 min. The reaction mixtures were cooled to room temperature, filtrated and pooled before the volatiles were evaporated. Purification by flash column chromatography (ethyl acetate/methanol, 1:0 to 1:1) gave the title compound (2.14 g, 87%). The amine was converted to the hydrochloric acid salt and re-crystallized from methanol/diethyl ether: M.p. 191° C. MS m/z (relative intensity, 70 eV) 275 (M+, 2), 246 (32), 73 (5), 72 (bp), 56 (11).

Example 2

N-[2-(3-FLUORO-5-METHYLSULFONYL-PHENOXY)ETHYL]BUTAN-1-AMINE

Preparation according to Example 1 but performed in one portion: 1-(2-bromoethoxy)-3-fluoro-5-methylsulfonyl-benzene (0.3 g, 1.01 mmol) and butan-1-amine (0.61 ml, 0.5907 mmol) in ethanol (4 ml). Yield: 290 mg (99%). The amine was converted to the hydrochloric acid salt and re-crystallized from ethanol/diethyl ether: M.p. 204° C. MS m/z (relative intensity, 70 eV) 289 (M+, 1), 246 (35), 86 (bp), 56 (12), 87 (12).

Example 3

N-ETHYL-2-(3-FLUORO-5-METHYLSULFONYL-PHENOXY)ETHANAMINE

Preparation according to Example 1 but performed in one portion: 1-(2-bromoethoxy)-3-fluoro-5-methylsulfonyl-benzene (0.321 g, 1.08 mmol) and ethanamine (4.3 ml, 8.6 mmol 2 M in methanol) in ethanol (6 ml). Yield: 255 mg (90%). The amine was converted to the hydrochloric acid salt and re-crystallized from ethanol/diethyl ether: M.p. 200.8-201.1° C. MS m/z (relative intensity, 70 eV) 261 (M+, 3), 94 (6), 59 (12), 58 (bp), 56 (8).

Example 4

N-[2-(3-FLUORO-5-METHYLSULFONYL-PHENOXY)ETHYL]-N-METHYL-PROPAN-1-AMINE

A mixture of Example 1 (0.54 g, 1.95 mmol) in formic acid (5.75 ml) and formaldehyde (40% solution, 5.1 ml) was heated at 85° C. for 5 h. The solution was allowed to reach ambient temperature, water (5 ml) and diethyl ether was added, the phases were separated and the aqueous phase was basified by the addition of aqueous sodium hydroxide (5 M). The aqueous phase was extracted twice with ethyl acetate, the combined organic phases were dried ($Na_2SO_4$) and evaporated under pressure to give the crude product which was then purified by flash chromatography (EtOAc:MeOH 100:0 then gradually changed to 0:100. The amine was converted to the hydrochloric acid salt and re-crystallized from methanol/diethyl ether: M.p. 128-130° C. MS m/z (relative intensity, 70 eV). 289 (M+, 1), 260 (26), 87 (6), 86 (bp), 58 (6).

Example 5

N-[2-(3-FLUORO-5-METHYLSULFONYL-PHENOXY)ETHYL]BUTAN-2-AMINE

Preparation according to Example 1 but performed in one portion: 1-(2-bromoethoxy)-3-fluoro-5-methylsulfonyl-benzene (0.5 g, 1.68 mmol) and sec-butylamine 1.37 ml, 13.46 mmol) in ethanol (5 ml). Purification by flash column chromatography (ethyl acetate/methanol, 100:0 to 85:15) gave the title compound (342 mg, 70%). The amine was converted to the hydrochloric acid salt and re-crystallized from methanol/diethyl ether: M.p. 166.5° C. MS m/z (relative intensity, 70 eV) 289 (M+, 1), 261 (25), 260 (bp), 86 (49), 70 (12).

Example 6

N-[2-(3-FLUORO-5-METHYLSULFONYL-PHENOXY)ETHYL]CYCLOPENTANAMINE

Preparation according to Example 1 but performed in one portion: 1-(2-bromoethoxy)-3-fluoro-5-methylsulfonyl-benzene (0.5 g, 1.68 mmol) and cyclopentylamine (1.34 ml, 13.46 mmol) in ethanol (5 ml). Purification by flash column chromatography (ethyl acetate/methanol, 100:0 to 85:15) gave the title compound (443 mg, 87.4%). The amine was converted to the hydrochloric acid salt and re-crystallized from methanol/diethyl ether: M.p. 207.5° C. MS m/z (relative intensity, 70 eV) 301 (M+, 2), 272 (7), 99 (24), 98 (bp), 70 (7).

Example 7

N-[2-(3-FLUORO-5-METHYLSULFONYL-PHENOXY)ETHYL]-2-METHYL-BUTAN-2-AMINE

Preparation according to Example 1 but performed in one portion: 1-(2-bromoethoxy)-3-fluoro-5-methylsulfonyl-benzene (0.5 g, 1.68 mmol) and tert-amylamine (1.61 ml, 13.46 mmol) in ethanol (5 ml). Purification by flash column chromatography (ethyl acetate/methanol, 100:0 to 85:15) gave the title compound (389 mg, 76.2%). The amine was converted to the hydrochloric acid salt and re-crystallized from methanol/diethyl ether: M.p. 190.2° C. MS m/z (relative intensity, 70 eV) 303 (M+, 0), 288 (21), 276 (10), 275 (41), 274 (bp), 84 (10).

Example 8

N-[2-(3-FLUORO-5-METHYLSULFONYL-PHENOXY)ETHYL]CYCLOBUTANAMINE

Preparation according to Example 1 but performed in one portion: 1-(2-bromoethoxy)-3-fluoro-5-methylsulfonyl-benzene (0.5 g, 1.68 mmol) and cyclobutylamine (1.17 ml, 13.46 mmol) in ethanol (4 ml). Purification by flash column chromatography (ethyl acetate/methanol, 100:0 to 85:15) gave the title compound (400 mg, 82.7%). The amine was converted to the hydrochloric acid salt and re-crystallized from methanol/diethyl ether: M.p. 202° C. MS m/z (relative intensity, 70 eV) 287 (M+, 0), 260 (33), 259 (91), 216 (bp), 215 (23), 56 (73).

Example 9

N-[2-(3-FLUORO-5-METHYLSULFONYL-PHENOXY)ETHYL]PROPAN-2-AMINE

Preparation according to Example 1 but performed in one portion: 1-(2-bromoethoxy)-3-fluoro-5-methylsulfonyl-benzene (0.5 g, 1.68 mmol) and isopropylamine (1.15 ml, 13.46 mmol) in ethanol (4 ml). Purification by flash column chromatography (ethyl acetate/methanol, 100:0 to 85:15) gave the title compound (421 mg, 90.9%). The amine was converted to the hydrochloric acid salt and re-crystallized from methanol/diethyl ether: M.p. 173° C. MS m/z (relative intensity, 70 eV) 275 (M+, 4), 261 (16), 260 (41), 73 (32), 72 (bp).

Example 10

1-[2-(3-FLUORO-5-METHYLSULFONYL-PHENOXY)ETHYL]PIPERIDINE

Preparation according to Example 1 but performed in one portion: 1-(2-bromoethoxy)-3-fluoro-5-methylsulfonyl-benzene (0.5 g, 1.68 mmol) and piperidine (1.33 ml, 13.46 mmol) in ethanol (5 ml). Purification by flash column chromatography (ethyl acetate/methanol, 100:0 to 85:15) gave the title compound (480 mg, 94.7%). The amine was converted to the hydrochloric acid salt and re-crystallized from methanol/diethyl ether: M.p. 194.6° C. MS m/z (relative intensity, 70 eV) 301 (M+, 1), 99 (8), 98 (bp), 96 (4), 55 (5).

Example 11

N,N-DIETHYL-2-(3-FLUORO-5-METHYLSULFONYL-PHENOXY)ETHANAMINE

Preparation according to Example 1 but performed in one portion: 1-(2-bromoethoxy)-3-fluoro-5-methylsulfonyl-benzene (0.5 g, 1.68 mmol) and di-ethylamine (1.39 ml, 13.46 mmol) in ethanol (4 ml). Purification by flash column chromatography (ethyl acetate/methanol, 1:0 to 1:1) gave the title compound (300 mg, 61.6%). The amine was converted to the hydrochloric acid salt and re-crystallized from methanol/diethyl ether: M.p. 172.3° C. MS m/z (relative intensity, 70 eV) 289 (M+, 1), 274 (6), 87 (6), 86 (bp), 58 (5).

Example 12

N-[2-(3-CHLORO-5-METHYLSULFONYL-PHENOXY)ETHYL]PROPAN-1-AMINE

Preparation according to Example 1 but performed in one portion: 1-(2-bromoethoxy)-3-chloro-5-methylsulfonylbenzene (0.5 g, 1.59 mmol) and propane-1-amine (1.04 ml, 12.76 mmol) in ethanol (5 ml). Yield: 368 mg (79.1%). The amine was converted to the hydrochloric acid salt and re-crystallized from ethanol/diethyl ether: M.p. 195-197° C. MS m/z (relative intensity, 70 eV) 291 (M+, 1), 264 (8), 262 (22), 73 (9), 72 (bp).

Example 13

N-{2-[3-FLUORO-5-(METHYLSULFONYL)PHE-NOXY]ETHYL}-N-PROPYLAMINE D2

2-[3-Fluoro-5-(methylsulfonyl)phenoxy]ethanamine (0.3 g, 1.26 mmol), propyl 4-methylbenzenesulfonate D2 (1.04 ml, 12.76 mmol) and potassium carbonate (0.35 g, 2.52 mmol) in acetonitrile (10 ml). The mixture was heated under microwave radiation at 120° C. for 45 min. The reaction mixtures were cooled to room temperature, filtrated and pooled before the volatiles were evaporated. Purification by flash column chromatography (ethyl acetate/methanol, 1:0 to 1:1) gave the title compound (0.15 g, 44%). The amine was converted to the hydrochloric acid salt and re-crystallized from methanol/diethyl ether. MS m/z (relative intensity, 70 eV) 277 (M+, 2), 248 (26), 138 (3), 94 (3), 74 (bp).

Example 14

N-(CYCLOPROPYLMETHYL)-N-{2-[3-FLUORO-5-(METHYLSULFONYL)-PHENOXY]ETHYL}AMINE

Preparation according to Example 1 but performed in one portion: 1-(2-bromoethoxy)-3-fluoro-5-methylsulfonyl-benzene (0.05 g, 0.16 mmol) and aminomethylcyclopropane (0.11 ml, 1.3 mmol) in ethanol (5 ml). MS m/z (relative intensity, 70 eV) 287 (M+, 2), 246 (6), 138 (2), 84 (bp), 56 (14).

Example 15

N-{2-[3-FLUORO-5-(METHYLSULFONYL)PHE-NOXY]ETHYL}-N-ISOBUTYLAMINE

Preparation according to Example 1 but performed in one portion: 1-(2-bromoethoxy)-3-chloro-5-methylsulfonyl-benzene (0.05 g, 0.16 mmol) and isobutylamine (0.2 ml, 1.3 mmol) in ethanol (5 ml). MS m/z (relative intensity, 70 eV) 289 (M+, 1), 246 (bp), 138 (2), 86 (70), 56 (17).

Example 16

1-[2-(3-FLUORO-5-METHYLSULFONYL-PHE-NOXY)ETHYL]AZETIDINE 1-(2-bromoethoxy)-3-fluoro-5-methylsulfonyl-benzene (0.5 g, 1.6 mmol), azetidine (0.23 ml, 3.2 mmol) and potassium carbonate (0.58 g, 4.2 mmol) was dissolved in acetonitrile (10 ml). The mixture was heated in a sealed container at 30120° C. for 2 h. The reaction mixture was cooled to room temperature, $CH_2Cl_2$ (100 ml) was added, solids was filtered off and the volatiles were evaporated. The amine was converted to the fumaric acid salt and re-crystallized from metha-nol/diethyl ether. MS m/z (relative intensity, 70 eV) 273 (M+, 1), 94 (5), 82 (3), 71 (5), 70 (bp).

Example 17

1-(3-FLUORO-5-METHYLSULFONYL-PHE-NOXY)-N-PROPYL-PROPAN-2-AMINE

Sodium triacetoxyborohydride (1.16 g, 5.51 mmol) was added to a stirred mixture of 1-(3-fluoro-5-methylsulfonyl-phenoxy)propan-2-one (0.905 g, 3.67 mmol), propylamine (0.24 g, 4.04 mmol), acetic acid (0.5 g, 8.33 mmol) and molecular sieves (2 g, 4 Å, 4-8 mesh) in dry 1,2-dichloroethane (20 ml) the mixture was stirred at ambient temperature for 24 h, the suspension was filtrated and sodium carbonate (100 ml, 10% aqueous solution) was added. The aqueous phase was extracted with dichloromethane (3×50 ml). The combined organic phase was dried with $Na_2SO_4$ and evaporated. Purification on flash chromatography (ethyl acetate: methanol 1:0 to 4:1). 0.3 g, 28%. MS m/z (relative intensity, 70 eV) 289 (M+, 1), 260 (9), 152 (4), 87 (6), 86 (bp).

Example 18

2-(3-fluoro-5-methylsulfonyl-phenoxy)-N-propyl-propan-1-amine

Toluenesulfonyl chloride (0.60 g, 3.1 mmol) was added to a stirred mixture of 4-dimethylaminopyridine (0.41 g, 3.4 mmol), triethylamine (0.53 g, 5.26 mmol) and a mixture of 1-(3-fluoro-5-methylsulfonyl-phenoxy)propan-2-ol and 2-(3-fluoro-5-methylsulfonyl-phenoxy)propan-1-ol (0.65 g, 2.63 mmol) in dry dichloromethane (20 ml). The resulting mixture was stirred at ambient temperature for 5 h, HCl (100 ml, 5% aqueous solution) was added, the aqueous phase was extracted with dichloro-methane (2×50 ml), the combined organic phase was washed with Brine (50 ml) and sodium carbonate (50 ml, 5% aqueous solution).

The resulting oil was dissolved in ethanol (5 ml) and methanol (5 ml) and propylamine (3.24 ml, 39.51 mmol) was added, the resulting mixture was heated to reflux for 15 h. The crude mixture was concentrated under vacuum and purified on flash chromatography (ethyl acetate:methanol 1:0 to 5:1). 0.52 g (as a mixture of 2-(3-fluoro-5-methylsulfonyl-phe-noxy)-N-propyl-propan-1-amine and 1-(3-fluoro-5-methyl-sulfonyl-phenoxy)-N-propyl-propan-2-amine), 68%. MS m/z (relative intensity, 70 eV) 289 (M+, 1), 260 (3), 73 (5), 72 (bp), 70 (9).

Preparations

Preparation 13-FLUORO-5-METHYLSULFONYL-PHENOL

Nitrogen was bubbled through a solution of 3-bromo-5-fluorophenol (10 g, 51.31 mmol) in dry dimethyl sulfoxide (70 ml) for 10 min after which sodium methanesulfinate (8.27 g, 76.96 mmol), cupper(I)iodide (5.86 g, 30.79 mmol), L-proline (7.09 g, 61.57 mmol) and potassium carbonate (4.25 g, 30.79 mmol) was added. The nitrogen flow was continued for an additional 10 min after which the mixture was heated at 100° C. for 24 h. Ethyl acetate (100 ml) and water (100 ml) was added and the phases were separated. The aqueous phase was extracted with ethyl acetate (2×100 ml), the combined organic phase was washed with aqueous lithium chloride (100 ml, 5%) and aqueous hydrochloric acid (100 ml, 5%), dried ($Na_2SO_4$) and evaporated. Purification by flash column chromatography (ethyl acetate/isooctane, 0:1 to 1:1) gave the title compound (7.17 g, 73%). MS m/z (relative intensity, 70 eV) 190 (M+, 81), 175 (27), 128 (50), 111 (bp), 83 (58).

Preparation 2

1-(2-BROMOETHOXY)-3-FLUORO-5-METHYL-SULFONYL-BENZENE

A mixture of 3-fluoro-5-methylsulfonyl-phenol (4.2 g, 22.08 mmol), 1,2-dibromoethane (24 ml, 27.7 mmol) and potassium carbonate (6.1 g, 44.2 mmol) in acetonitrile (36 ml) was divided into 6 aliquots which were each heated under microwave radiation at 120° C. for 30 min. The reaction mixtures were cooled to room temperature, filtrated and pooled. The volatiles were evaporated, aqueous sodium carbonate (100 ml, 10%) was added and the mixture was extracted with ethyl acetate (2×100 ml). The combined organic phase was washed with brine (75 ml), dried ($Na_2SO_4$) and evaporated. Purification by flash column chromatography (ethyl acetate/isooctane, 0:1 to 1:0) gave the title compound (4.77 g, 73%). MS m/z (relative intensity, 70 eV 298 (M+, 18), 296 (M+, 18), 109 (bp), 107 (99), 82 (15).

Preparation 3

TERT-BUTYL 2-[3-FLUORO-5-(METHYLSULFONYL)PHENOXY]ETHYL-CARBAMATE

A mixture of triphenylphosphine (1.9 g, 7.3 mmol) in dry THF (20 ml) was flushed with $N_2(g)$ and DEAD (3.1 ml, 6.9 mmol) was added drop-wise, 1,2-dibromoethane followed by 3-fluoro-5-methylsulfonyl-phenol (1.1 g, 6.1 mmol) and then boc-glycinol (1.0 ml, 6.1 mmol) in portions. The mixture was stirred at 70° C. for 20 h, cooled to room temperature and water and EtOAc was added. The aqueous phase was extracted with ethyl acetate (2×100 ml). The combined organic phase was washed with aqueous NaOH (3 M, 50 ml) and brine (75 ml), dried ($Na_2SO_4$) and evaporated. Purification by flash column chromatography (ethyl acetate/isooctane, 0:1 to 1:0) gave the title compound (1.4 g, 70%). MS m/z (relative intensity, 70 eV 298 (M+, 18), 296 (M+, 18), 109 (bp), 107 (99), 82 (15).

Preparation 4

2-[3-FLUORO-5-(METHYLSULFONYL)PHENOXY]ETHANAMINE

A mixture of tert-butyl 2-[3-fluoro-5-(methylsulfonyl) phenoxy]ethyl-carbamate (1.4 g, 4.2 mmol) in EtOH (18 ml) was added HCl (1.25 M in EtOH, 6 ml). The mixture was stirred at ambient temperature for 20 h. The aqueous phase was made basic by addition of aqueous NaOH (1 M, 50 ml) and extracted with ethyl acetate (2×100 ml). The combined organic phase was washed with brine (75 ml), dried ($Na_2SO_4$) and evaporated to yield the title compound (0.77 g, 77%). MS m/z (relative intensity, 70 eV 298 (M+, 18), 296 (M+, 18), 109 (bp), 107 (99), 82 (15).

Preparation 5

3-CHLORO-5-METHYLSULFONYL-PHENOL

Preparation according to Preparation 1: 3-bromo-5-chlorophenol (4.0 g, 19.3 mmol), sodium methanesulfinate (3.1 g, 28.9 mmol), cupper(I)iodide (2.2 g, 11.5 mmol), L-proline (2.7 g, 23.1 mmol), potassium carbonate (1.6 g, 11.6 mmol), dry dimethyl sulfoxide (70 ml). Yield: 3.7 g (92%). MS m/z (relative intensity, 70 eV) 206 (M+, 88), 191 (36), 144 (58), 127 (bp), 99 (76).

Preparation 6

1-(2-BROMOETHOXY)-3-CHLORO-5-METHYL-SULFONYL-BENZENE

Preparation according to Preparation 2: 3-chloro-5-methylsulfonyl-phenol (2.8 g, 13.5 mmol), 1,2-dibromoethane (12 ml, 135 mmol), potassium carbonate (3.7 g, 27.1 mmol), acetonitrile (15 ml) Yield: 2.1 g, 50%). MS m/z (relative intensity, 70 eV 314 (M+, 35), 312 (M+, 25), 206 (7), 126 (9), 109 (98), 107 (bp).

Preparation 7

2-(3-fluoro-5-methylsulfonyl-phenoxy)propan-1-ol

A mixture of 1-bromo-2-propanol (70%) and 2-bromo-1-propanol (30%) (5.81 g, 41.8 mmol) was added to a solution of 3-fluoro-5-methylsulfonyl-phenol (1.59 g, 8.36 mmol) and potassium carbonate (2.37 g, 16.71 mmol) in dry dimethyl formamide (10 ml), the mixture was heated to 120° C. for 20 hours, the mixture was allowed to cool to ambient temperature and water (100 ml) was added. The aqueous phase was extracted with ethyl acetate (3×100 ml), the combined organic phase was washed with LiCl (5% aqueous solution, 4×50 ml), brine (50 ml) and dried with $Na_2SO_4$ and evaporated. Purification flash chromatography (isooctane: ethyl acetate 1:0 to 3:2). 0.65 g (mixture of 1-(3-fluoro-5-methylsulfonyl-phenoxy)propan-2-ol and 2-(3-fluoro-5-methylsulfonyl-phenoxy)propan-1-ol), 31%. MS m/z (relative intensity, 70 eV) 248 (M+, 14), 204 (54), 203 (bp), 191 (37), 190 (44).

Preparation 8

1-(3-fluoro-5-methylsulfonyl-phenoxy)propan-2-one

1-Chloroacetone (95%, 2.66 g, 27.34 mmol) was added to a stirred solution of 3-fluoro-5-methylsulfonyl-phenol (80%, 1.3 g, 5.46 mmol) and potassium carbonate (2.26 g, 16.40 mmol) in dry dimethyl formamide (10 ml), the mixture was heated to 120° C. for 20 minutes, the mixture was allowed to cool to ambient temperature and water (100 ml) was added. The aqueous phase was extracted with ethyl acetate (3×100 ml), the combined organic phase was washed with LiCl (5% aqueous solution, 4×50 ml), brine (50 ml) and dried with $Na_2SO_4$ and evaporated. Purification on flash chromatography (isooctane: ethyl acetate 1:0 to 3:2). 0.905 g, 67%. MS m/z (relative intensity, 70 eV) 246 (M+, 79), 204 (55), 203 (bp), 141 (30), 94 (67).

Biological Activity 3,4-dihydroxyphenyl-acetic acid (DOPAC) in the striatum

The increased turnover of dopamine in the terminal areas of the ascending dopaminergic projections of the mammalian brain can be illustrated by measuring of changes in biochemical indices in the brain with the characteristic features of dopamine antagonists, e.g. producing increases in concentrations of dopamine metabolites such as 3,4-dihydroxyphenylacetic acid (DOPAC) in the striatum.

Test results are shown in Table 1.

TABLE 1

Estimated $ED_{50}$ values on increase of DOPAC (3,4-dihydroxyphenylacetic acid) in the rat striatum after systemic administration of test compound. For methods and statistical calculations see the below test methods.

| Compound | $ED_{50}$ DOPAC (μmol/kg) |
|---|---|
| Example 1 | 8.5 (7.4-10.3) |
| Example 2 | 4.2 (3.5-5.3) |
| Example 4 | 28.1 (24.5-28.1) |
| Example 8 | 36 (25.6-51.1) |
| Example 10 | 14.5 (10.8-16.9) |
| Example 12 | 10.5 (7.7-15.6) |

Effects on Spontaneous Locomotion

Prior art dopamine receptor antagonists are known to induce profound decrease in locomotor activity (catalepsy). Effects of a compound of the invention on spontaneous locomotion are shown in Table 2.

TABLE 2

Effects of a compound of the invention on Locomotor activity in drug-naive rats. The animals were placed in the motility meters immediately after drug administration and locomotor activity was recorded for 60 minutes (counts/60 min ± SEM).

| Compound | Control group | 3.7 μmol/kg | 11 μmol/kg | 33 μmol/kg |
|---|---|---|---|---|
| Example 1 | 6414 | 8049 | 7325 | 6025 |
| Example 2 | 14161 | 13941 | 8617 | 6325 |
| Example 4 | 13890 | 11435 | 10025 | 12829 |
| Example 8 | 13633 | 10319 | 12888 | 12872 |
| Example 10 | 9816 | 11979 | 9344 | 8144 |
| Example 12 | 13630 | 14414 | 12740 | 7826 |

Amphetamine-Induced Hyper-Locomotion

The increase in activity after treatment with d-amphetamine is a standard model of hyperdopaminergia. In this model, dopaminergic neurotransmission is increased by systemic administration of d-amphetamine at a dose that is sufficiently high to produce a large increase in locomotor activity. The ability of a compound to antagonize this hyperactivity reflects anti-dopaminergic properties. Furthermore, antagonism of d-amphetamine induced hyperactivity is widely used as a standard assay of antipsychotic activity (see *Psychopharmacology* 4th *Generation of progress* Chapter 68, p 793-795).

The effects of a compound of the invention on the increase in activity induced by direct or indirect dopaminergic agonists, i.e. d-amphetamine and congeners are shown in Table 3.

TABLE 3

Effect of compound of the present invention on reduction of amphetamine-induced hyper-locomotion. For methods and statistical calculations see the below test methods.

| Compound | $ED_{50}$ μmol/kg |
|---|---|
| Example 1 | 24 (18-30) |

TABLE 3-continued

Effect of compound of the present invention on reduction of amphetamine-induced hyper-locomotion. For methods and statistical calculations see the below test methods.

| Compound | $ED_{50}$ μmol/kg |
|---|---|
| Example 4 | 69 (24-290) |

Reduction of MK-801-Induced Hyper-Locomotion

Another animal model of antipsychotic activity is based on administration of the glutamate antagonist MK-801. Glutamate antagonists (i.e. NMDA antagonists), can induce psychoses in man (see *Psychopharmacology*, 4th *Generation of progress* Chapter 101, p. 1205 and 1207) and induce behavioural aberrations in animals. Thus, the ability of a drug to affect schizophrenia and psychotic states can be measured using behavioural models based on experimentally-induced hypoglutamatergic states. In this study the NMDA antagonist MK-801 (0.7 mg/kg i.p.) was used to create a hypoglutamatergic state where the rats display abnormal, hyperactive behaviour.

Test results for a compound of the present invention are seen in Table 4.

TABLE 4

Effect of compound of the present invention on reduction of MK-801-induced hyper-locomotion (0.7 mg/kg i.p. 90 minutes before test compound). For methods and statistical calculations see the below test methods. The animals were placed in the motility meters immediately after test compound administration and locomotor activity was recorded between 45 and 60 minutes after administration (counts/15 min ± SEM)

| Compound | $ED_{50}$ μmol/kg |
|---|---|
| Example 1 | 5.6 (0.3-18) |
| Example 8 | 40 (20-100) |

Increase of Arc Gene Expression

It is known that the dopaminergic systems of the brain interact strongly with other transmitter systems (see *Psychopharmacology*, 4th *Generation of progress*, Chapter 101, pages 1208-1209).

To investigate potential effects of compounds of the present invention on cortical and striatal NMDA receptor related synaptic signaling, Arc mRNA induction was assessed upon acute administration of a compound of the present invention. Arc (Arc/Arg3.1-activity regulated cytoskeleton-associated protein/activity-regulated gene 3.1; (Link W et al.; *Proc Natl Acad Sci USA* 1995 92 5734-5738; Lyford G L et al; *Neuron* 1995 14 433-445)), is an immediate early gene (IEG), induced by synaptic activity, whose expression and localization at synaptic sites is triggered specifically by NMDA receptor activation and strongly related to neural plasticity (Steward O, Worley P F; *Neuron* 2001 30 227-240; Takashi Kawashima et al.; *PNAS* 2009 106 (1) 316-321; Clive R. Bramham et al.; *Exp. Brain Res.* 2010 200 125-140).

Test results for a compound of the invention are shown in Table 5.

TABLE 5

Estimated $ED_{50}$ values on increase of Arc gene expression in the rat striatum and cortex after systemic administration of test compound. For methods and statistical calculations see the below test methods.

| Compound | $ED_{50}$ Arc (μmol/kg) |
| --- | --- |
| Example 1 (striatum) | 13 (5.6-77) |
| Example 1 (Cortex) | <11 |

Test Methods

The following tests are used for evaluation of the compounds according to the invention.

In Vivo Test: Behaviour

Behavioural activity is measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB D10-24, National Instruments, USA). Each activity monitor consists of a quadratic metal frame (W×L=40 cm×40 cm) equipped with photobeam sensors. During measurements of behavioural activity, a rat is put in a transparent acrylic cage (W×L×H, 40×40×30 cm) which in turn is placed in the activity monitor. Each activity monitor is equipped with three rows of infrared photobeam sensors, each row consisting of 16 sensors. Two rows are placed along the front and the side of the floor of the cage, at a 90° angle, and the third row is placed 10 cm above the floor to measure vertical activity. Photobeam sensors are spaced 2.5 cm apart. Each activity monitor is fitted in an identical sound and light attenuating box containing a weak house light and a fan.

The computer software is written using object oriented programming (LabVIEW®, National instruments, Austin, Tex., USA).

Behavioural data from each activity monitor, representing the position (horizontal center of gravity and vertical activity) of the animal at each time, are recorded at a sampling frequency of 25 Hz and collected using a custom written LABView™ application. The data from each recording session are stored and analyzed with respect to distance traveled. Each behavioural recording session lasts 60 min, starting approximately 4 min after the injection of test compound. Similar behavioural recording procedures are applied for drug-naïve and drug pre-treated rats. Rats pre-treated with d-amphetamine are given a dose of 1.5 mg/kg i.p. 10 min before the recording session in the activity monitor. Rats pre-treated with MK-801 are given a dose of 0.7 mg/kg i.p. 90 min before the recording session in the activity monitor. The results are presented as counts/60 minutes, or counts/30 minutes, in arbitrary length units. Statistical comparisons are carried out using Student's t-test against the control group. In MK-801 or amphetamine pre-treated animals, statistical comparisons are made against the MK801 or d-amphetamine controls, respectively.

$ED_{50}$ value for reduction of amphetamine-induced hyperlocomotion is calculated by curve fitting. The evaluation is based on 16 amphetamine pre-treated animals over the dose range 0, 11, 33 and 100 μmol/kg s.c. in one single experiment. Calculations are based on distance during the last 45 minutes of one hour of measurement. The distances are normalised to amphetamine-control and fitted by least square minimization to the function "End-(End-Control)/(1+(dose/$ED_{50}$)$^{Slope}$)". The four parameters (Control, End, $ED_{50}$ and Slope) are fitted with the restrictions: $ED_{50}>0$, $0.5<\text{Slope}<3$, End=0% of control. The restriction with locked End is made to focus on potency rather than efficacy. To estimate confidence levels for the parameters, the fit is repeated 100 times with a random evenly distributed squared weight (0 to 1) for every measurement value. Presented $ED_{50}$-ranges cover 95% of these values.

$ED_{50}$ value for reduction of MK-801-induced hyper-locomotion is calculated by curve fitting. The evaluation is based on 16 MK-801 pre-treated animals over the dose range 0, 11, 33 and 100 μmol/kg s.c. in one single experiment. Calculations are based on distance during the last 15 minutes of one hour of measurement. The distances are normalised to MK-801-control and fitted by least square minimization to the function "End-(End-Control)/(1+(dose/$ED_{50}$)$^{Slope}$)". The four parameters (Control, End, $ED_{50}$ and Slope) are fitted with the restrictions: $ED_{50}>0$, $0.5<\text{Slope}<3$, End=0% of control. The restriction with locked End is made to focus on potency rather than efficacy. To estimate confidence levels for the parameters, the fit is repeated 100 times with a random evenly distributed squared weight (0 to 1) for every measurement value. Presented $ED_{50}$-ranges cover 95% of these values.

In Vivo Test: Neurochemistry

After the behavioural activity sessions, the rats are decapitated and their brains rapidly taken out and put on an ice-cold petri-dish. The limbic forebrain, the striatum, the frontal cortex and the remaining hemispheral parts of each rat are dissected and frozen. Each brain part is subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 μm, 50×2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% v/v), decane sulfonic acid 0.45 mM, and EDTA 0.1 mM. Detection potentials relative to Ag/AgCl reference are 0.45 and 0.65V.

$ED_{50}$ value for the increase of DOPAC in striatum is calculated by curve fitting. The evaluation is based on 40 animals over the dose range 0, 3.7, 11, 33 and 100 μmol/kg s.c. in two combined experiments. The DOPAC levels are normalised to control and fitted by least square minimization to the function "End-(End-Control)/(1+(dose/$ED_{50}$)$^{Slope}$)". The four parameters (Control, End, $ED_{50}$ and Slope) are fitted with the restrictions: $ED_{50}>0$, $0.5<Slope<3$, $350<End<400\%$ of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Oral Bioavailability

Experiments are performed 24 hours after implantation of arterial and venous catheters. Test compound is administered orally at 12.5 μmol/kg or intravenously at 5 μmol/kg using the venous catheters, n=3 per group. Arterial blood samples are then taken during six hours at 0, 3, 9, 27, 60, 120, 180, 240, 300 and, 360 minutes after administration of the test compound. The oral bioavailability is calculated as the ratio of the AUC (Area under curve) obtained after oral administration over the AUC obtained after intravenous administration for each rat. The parameter AUC is calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings:MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V.

Analytical column: Zorbax eclipse XDB-C8 (4.6×150 mm, 5 μm) at 20° C. The mobile phase is acetic acid (0.03%) (solvent A) and acetonitrile (solvent B). The flow rate of the mobile phase is 0.8 ml/min. The elution is starting at 12% of solvent β isocratic for 4.5 min, then increasing linearity to 60% over 4.5 min.

Extractions procedure: Plasma samples (0.25-0.5 ml) are diluted with water to 1 ml, and 60 μmol (100 μl) internal standard (−)-OSU6241 is added. The pH was adjusted to 11 by the addition of 25 μl saturated $Na_2CO_3$. After mixing, the samples are extracted with 4 ml dichloromethane by shaking for 20 min. The organic layer is after centrifugation transferred to a smaller tube and evaporated to dryness under a stream of nitrogen. The residue is then dissolved in 120 μl mobile phase (acetic acid (0.03%): acetonitrile, 95:5) for LC-MS analysis (10 μl injected). The selective ion ($MH^+$) is monitored for each example, and $MH^+$296 for (−)-OSU6241 ((3-[3-(ethylsulfonyl)phenyl]-1-propylpiperidine).

A standard curve over the range of 1-500 μmol is prepared by adding appropriate amounts of test compound to blank plasma samples.

In Vitro Test: Metabolic Stability in Rat Liver Microsomes

Rat liver microsomes are isolated as described by Förlin [Förlin L: *Tox Appl Pharm*. 54 (3) 420-430, 1980] with minor modifications e.g. 3 ml/g liver of a 0.1 M Na/K*$PO_4$ buffer with 0.15M KCl, pH 7.4, (buffer 1) is added before homogenisation, the homogenate is centrifuged for 20 minutes instead of 15, the supernatant is ultracentrifuged at 100.000 g instead of 105.000 g and the pellet from the ultracentrifugation is resuspended in 1 ml/g liver of 20% v/v 87% glycerol in buffer 1.

1 μL of, 0.2 or 1 mM test substance diluted in water, and 10 μL 20 mg/ml rat liver microsome are mixed with 149 μL 37° C. buffer 1 and the reaction is started by addition of 40 μL 4.1 mg/ml NADPH. After 0 or 15 minutes incubation at 37° C. in a heating block (LAB-LINE, MULTI-BLOK Heater or lab4you, TS-100 Thermo shaker at 700 rpm) the reaction is stopped by addition of 100 μL pure acetonitrile. The protein precipitation is then removed by rejecting the pellet after centrifugation at 10.000 g for 10 minutes (Heraeus, Biofuge fresco) in 4° C. The test compound is analysed using HPLC-MS (Hewlett-Packard 1100MSD Series) with a Zorbax SB-C18 column (2.1×150 mm, 5 μm) using 0.03% formic acid and acetonitrile as mobile phase (gradient) or a Zorbax Eclipse XDB-C18 (3×75 mm, 3.5 μm) using 0.03% acetic acid and acetonitrile as mobile phase (gradient). The 15 min turnover is calculated as the fraction of test compound eliminated after 15 minutes, expressed in percent of 0 min levels, i.e. 100×[conc test compound at 0 min−concentration at 15 min]/conc at 0 min.

Preparation of liver microsomes is performed as described in Förlin [Förlin L: *Tox Appl Pharm*. 54, (3) 420-430, 1980]. Protocols for incubation with liver microsomes are referred in Crespi et Stresser [Crespi C L, DM Stressser *J. Pharm. Tox. Meth*. 44 325-331, 2000], and Renwick et al [Renwick A B et al.; *Xenobiotica* 2001 31 (4) 187-204].

Microdialysis

Male Sprague-Dawley rats weighing 220-320 g are used throughout the experiments. Before the experiment the animals are group housed, five animals in each cage, with free access to water and food. The animals are housed at least one week after arrival prior to surgery and use in the experiments. Each rat is used only once for microdialysis.

We use a modified version of Waters et al. [Waters et al.; *J. Neural. Transm. Gen. Sect*. 1994 98 (1) 39-55] of the I-shaped probe as described by Santiago and Westerink [Santiago M, Westerink BHC; *Naunyn-Schmiedeberg's Arch. Pharmacol*. 1990 342 407-414]. The dialysis membrane we use is the AN69 polyacrylonitrile/sodiummethalylsulfonate copolymer (HOSPAL; o.d./i.d. 310/220 μm: Gambro, Lund, Sweden). In the dorsal striatum we use probes with an exposed length of 3 mm of dialysis membrane and in the prefrontal cortex the corresponding length is 2.5 mm. The rats are operated under isoflurane inhalationanesthesia while mounted into a Kopf stereotaxic instrument. Coordinates are calculated relative to bregma; dorsal striatum AP+1, ML±2.6, DV−6.3; Pf cortex, AP+3.2, 8° ML±1.2, DV−4.0 according to Paxinos and Watson [Paxinos G, Watson C: The Rat Brain in Stereotaxic Coordinates; New York, Academic Press 1986]. The dialysis probe is positioned in a burr hole under stereotaxic guidance and cemented with phosphatine dental cement.

The rats are housed individually in cages for 48 h before the dialysis experiments, allowing them to recover from surgery and minimizing the risk of drug interactions with the anaesthetic during the following experiments. During this period the rats have free access to food and water. On the day of experiment the rats are connected to a micro perfusion pump via a swiwel and are replaced in the cage where they can move freely within its confinements. The perfusion medium is a Ringer's solution containing in mmol/l: NaCl; 140, $CaCl_2$; 1.2, KCl; 3.0, $MgCl_2$; 1.0 and ascorbic acid; 0.04 according to Moghaddam and Bunney [Moghaddam B, Bunney B S; *J. Neurochem*. 1989 53 652-654]. The pump is set to a perfusion speed of 2 μl/min and 40 μl samples are collected every 20 min.

Each sample is analyzed at two HPLC systems. On an autoinjector (CMA 200) with a 10-port valve (Valco C10WE), holding two sample loops in series (4 μl and 20 μl), each brain dialysate sample is loaded in both loops simultaneously. At injection the 20 μl sample is introduced into a column switching system (reverse-phase combined with reverse-phase ion-pairing) for dopamine (DA), noradrenaline (NA), normetanephrine (NM), 3-methoxytyramine (3-MT) and serotonin (5-hydroxytryptamine, 5-HT) determination, while the 4 µl sample is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromeleon software (Dionex) on a PC. The method sample turn over time is 4.5 min and two parallel experiments are normally analyzed simultaneously on the system. After the experiment the rats are uncoupled from the perfusion pump and decapitated. Their brains are rapidly taken out and fixed in Neo-fix solution (Kebo-lab, Sweden) for subsequent inspection of probe localisation. The Animal Ethics Committee in Göteborg, Sweden approved the procedures applied in these experiments.

PCR

Total RNA is prepared by the guanidin isothiocyanate method reported by Chomczynski & Sacchi [Chomczynski P & Sacchi N; *Anal. Biochem.* 1987 162 156-159]. RNA pellets are solved in MQ water and stored at −80° C. The sample concentration was determined spectrophotometrically by a NanoDrop ND-1000. A quality indicator number and an integrity number of r-RNA were measured with an Experion (Bio-Rad) on random samples.

Reversed transcription was performed by using a SuperScript III kit (Invitrogen). 1 µg of total RNA was reverse transcribed with 5 µl 2×RT Reaction Mix, 1 µl RT Enzyme Mix, volume adjusted to 10 µl with DEPC-treated water. 1U of *E. coli* RNase H was added. cDNA was diluted 40 times and stored at −20° C.

For real-time PCR measurements, 0.7 µl of the cDNA reaction was amplified in a 25 µl reaction mixture containing 1×PCR buffer, 0.2 mM dNTP, 3.7 mM $MgCl_2$, 0.15 mM SYBR green, 0.4 µM of each primer, and 1U JumpStart Taq DNA polymerase. Real-time PCR was measured on CFX96 (Biorad) using the following settings for all genes, 60 s pre-incubation at 95° C., followed by 40 cycles of denaturation at 95° C. for 10 s, annealing at 56° C. for 10 s, and elongation at 72° C. for 10 s.

The primer sequences were as follows:

```
Hypoxanthine phosphoribosyl transferase (HPRT)
(Accession Number AF001282)
                                        (SEQ ID NO: 1)
Sense: 5'-GGC CAG ACT TGT TGG ATT TG-3'
                                        (SEQ ID NO: 2)
Antisense: 5'-CCG CTG TCT TTT AGG CTT TG-3'

Cyclophilin A (Accession Number M19533)
                                        (SEQ ID NO: 3)
Sense: 5'-GTC TCT TTT CGC CGC TTG CT-3'
                                        (SEQ ID NO: 4)
Antisense: 5'-TCT GCT GTC TTT GGA ACT TTG TCT G-3'

Activity-regulated gene (Arc)
(Accession Number U19866)
                                        (SEQ ID NO: 5)
Sense: 5'-GTC CCA GAT CCA GAA CCA CA-3'
                                        (SEQ ID NO: 6)
Antisense: 5'-CCT CCT CAG CGT CCA CAT AC-3'
```

Initial DNA amounts were quantified by a standard curve constructed for every gene using 6 serial 4-fold dilutions of purified PCR products. Correct PCR products were confirmed by agarose gel electroforesis (2%) PCR products were purified with PCR purification kit from Qiagen (Valencia, Calif., USA) All genes were sequenced at MWG, Germany, and routinely by melting curve analysis.

Arc gene amounts were normalised using the geometric mean of the amounts of the two house-keeping genes assessed (HPRT and cyclophilin A).

$ED_{50}$ value for the increase of Arc in striatum is calculated by curve fitting. The evaluation is based on 20 animals over the dose range 0, 11, 33 and 100 µmol/kg s.c. in a single experiments. The Arc levels are normalised to control and fitted by least square minimization to the function "End−(End−Control)/(1+(dose/$ED_{50}$)$^{Slope}$)". The four parameters (Control, End, $ED_{50}$ and Slope) are fitted with the restrictions: $ED_{50}>0$, $0.5<Slope<3$, $300<End<600\%$ of control. To estimate confidence levels for the parameters, the fit is repeated 100 times with a random evenly distributed squared weight (0 to 1) for every measurement value. Presented $ED_{50}$-ranges cover 95% of these values.

$ED_{50}$ value for the increase of Arc in (prefrontal) cortex is evaluated to be clearly below the lowest dose.

The invention claimed is:

1. A phenoxy-ethyl-amine derivative of Formula 1

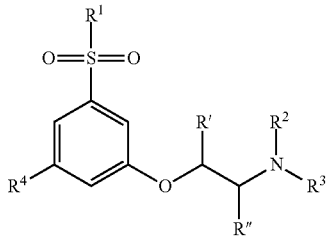

(1)

a stereoisomer or a mixture of its stereoisomers, or an N-oxide thereof, or a deuterated analog thereof, or a pharmaceutically acceptable salt thereof, wherein $R^1$ represents $CH_3$ or $CF_3$;

$R^2$ is selected from the group consisting of $C_1$-$C_4$-alkyl, allyl, $CH_2CH_2OCH_3$, $C(CH_3)_2CH_2CH_3$, $CH_2$-cyclopropyl, cyclobutyl, cyclopentyl, $CH_2CH_2CH_2F$, $CH_2CH_2CHF_2$, $CH_2CH_2F$, 3,3,3-trifluoropropyl and 4,4,4-trifluorobutyl; and $R^3$ is selected from the group consisting of H, $CH_3$ and $CH_2CH_3$; or $R^2$ and $R^3$ together form $CH_2(CH_2)CH_2$ or $CH_2(CH_2)_3CH_2$;

$R^4$ represents F or Cl; and

R' and R" independently represent hydrogen or methyl.

2. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein $R^1$ represents $CH_3$.

3. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein $R^2$ is selected from the group consisting of $C_1$-$C_4$-alkyl, $C(CH_3)_2CH_2CH_3$, $CH_2$-cyclopropyl, cyclobutyl, and cyclopentyl.

4. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein $R^3$ is selected from the group consisting of H and $CH_3$.

5. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein $R^2$ and $R^3$ together form $CH_2(CH_2)CH_2$ or $CH_2(CH_2)_3CH_2$.

6. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein $R^4$ represents F.

7. The phenoxy-ethyl-amine derivative according to claim 1, a stereoisomer or a mixture of its stereoisomers, or an N-oxide thereof, or a deuterated analog thereof, or a pharmaceutically acceptable salt thereof, wherein R' and R" independently represent hydrogen.

8. The phenoxy-ethyl-amine derivative according to claim 1, wherein the phenoxy-ethyl-amine derivative is
   N-[2-(3-Fluoro-5-methylsulfonyl-phenoxy)ethyl]propan-1-amine;
   N-[2-(3-Fluoro-5-methylsulfonyl-phenoxy)ethyl]butan-1-amine;
   N-ethyl-2-(3-fluoro-5-methylsulfonyl-phenoxy)ethanamine;
   N-[2-(3-Fluoro-5-methylsulfonyl-phenoxy)ethyl]-N-methyl-propan-1-amine;
   N-[2-(3-Chloro-5-methylsulfonyl-phenoxy)ethyl]propan-1-amine;
   N-[2-(3-Fluoro-5-methylsulfonyl-phenoxy)ethyl]butan-2-amine;
   N-[2-(3-Fluoro-5-methylsulfonyl-phenoxy)ethyl]cyclopentanamine;
   N-[2-(3-Fluoro-5-methylsulfonyl-phenoxy)ethyl]-2-methyl-butan-2-amine;
   N-[2-(3-Fluoro-5-methylsulfonyl-phenoxy)ethyl]cyclobutanamine;
   N-[2-(3-Fluoro-5-methylsulfonyl-phenoxy)ethyl]propan-2-amine;
   1-[2-(3-Fluoro-5-methylsulfonyl-phenoxy)ethyl]piperidine;
   N,N-Diethyl-2-(3-fluoro-5-methylsulfonyl-phenoxy)ethanamine;
   N-1,1-di-deuterium-propyl-[2-(3-fluoro-5-methanesulfonyl-phenoxy)-ethyl]-amine;
   N-(Cyclopropylmethyl)-N-{2-[3-fluoro-5-(methylsulfonyl)-phenoxy]ethyl}amine;
   N-{2-[3-Fluoro-5-(methylsulfonyl)phenoxy]ethyl}-N-isobutylamine;
   1-[2-(3-Fluoro-5-methylsulfonyl-phenoxy)ethyl]azetidine;
   1-(3-Fluoro-5-methylsulfonyl-phenoxy)-N-propyl-propan-2-amine; or
   2-(3-Fluoro-5-methylsulfonyl-phenoxy)-N-propyl-propan-1-amine;
   a stereoisomer or a mixture of its stereoisomers, or an N-oxide thereof, or a deuterated analog thereof, or a pharmaceutically acceptable salt thereof.

9. The phenoxy-ethyl-amine derivative according to claim 1, wherein the phenoxy-ethyl-amine derivative is N-[2-(3-fluoro-5-methylsulfonyl-phenoxy)ethyl]propan-1-amine, a stereoisomer or a mixture of its stereoisomers, or an N-oxide thereof, or a deuterated analog thereof, or a pharmaceutically acceptable salt thereof.

10. A pharmaceutical composition, comprising a therapeutically effective amount of a phenoxy-ethyl-amine derivative of claim 1, a stereoisomer or a mixture of its stereoisomers, or an N-oxide thereof, or a deuterated analog thereof, or a pharmaceutically acceptable salt thereof, together with at least one pharmaceutically acceptable carrier or diluent.

11. A method of treatment of a disease or a disorder or a condition of a patient, which disorder, disease or condition is selected from the group of psychosis, schizophrenia, schizophreniform disorder, bipolar disorder, anxiety disorder, depression, obsessive-compulsive disease, dementia, age-related cognitive impairment, Autism spectrum disorders, attention deficit hyperactivity disorder (ADHD), Gilles de la Tourette's syndrome, eating disorder, Parkinson's disease, parkinsonian syndrome, L-3,4-dihydroxyphenylalanine (L-DOPA) induced dyskinesia, Tardive dyskinesia, dystonia, Huntington's disease, and Alzheimer's disease, which method comprises the step of administering to such a patient in need thereof a therapeutically effective amount of a phenoxy-ethyl-amine derivative of claim 1, a stereoisomer or a mixture of its stereoisomers, or an N-oxide thereof, or a deuterated analog thereof, or a pharmaceutically acceptable salt thereof.

12. The method of claim 11, wherein the disease, disorder or condition is selected from the group of psychosis, schizophrenia, schizophreniform disorder, bipolar disorder, depression, obsessive-compulsive disease, dementia, age-related cognitive impairment, Autism spectrum disorders, Gilles de la Tourette's syndrome, eating disorder, and Huntington's disease.

13. The method of claim 11, wherein the disease, disorder or condition is selected from the group of schizophrenia, L-DOPA induced dyskinesia, and Huntington's disease.

14. The method of claim 11, wherein the disease, disorder or condition is L-DOPA induced dyskinesia.

15. The method of claim 11, wherein the patient is a human.

16. A method of treatment of a disease or a disorder or a condition of a patient, which disorder, disease or condition is selected from the group of drug induced psychotic disorder, mood disorder, dyskinesia, tics and tremor dementia, and dementia disorder related to Alzheimer's disease, which method comprises the step of administering to such a patient in need thereof a therapeutically effective amount of a phenoxy-ethyl-amine derivative of claim 1, a stereoisomer or a mixture of its stereoisomers, or an N-oxide thereof, or a deuterated analog thereof, or a pharmaceutically acceptable salt thereof.

17. A method of treatment of psychotic disorder of a patient, which method comprises the step of administering to such a patient in need thereof a therapeutically amount of a phenoxy-ethyl-amine derivative of claim 1, a stereoisomer or a mixture of its stereoisomers, or an N-oxide thereof, or a deuterated analog thereof, or a pharmaceutically acceptable salt thereof.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: synthetic construct; sense primer for HPRT

<400> SEQUENCE: 1
ggccagactt gttggatttg                                          20

<210> SEQ ID NO 2
<211> LENGTH: 20
<212> TYPE: DNA
<213> ORGANISM: Artificial Sequence
<220> FEATURE:
<223> OTHER INFORMATION: synthetic construct; antisense primer for HPRT

<400> SEQUENCE: 2
ccgctgtctt ttaggctttg                                          20
```

```
<210> SEQ ID NO 3
<211> LENGTH: 20
<212> TYPE: DNA
<213> ORGANISM: Artificial Sequence
<220> FEATURE:
<223> OTHER INFORMATION: synthetic construct; sense primer for
      Cyclophilin A

<400> SEQUENCE: 3
gtctcttttc gccgcttgct                                              20

<210> SEQ ID NO 4
<211> LENGTH: 25
<212> TYPE: DNA
<213> ORGANISM: Artificial Sequence
<220> FEATURE:
<223> OTHER INFORMATION: synthetic construct; antisense primer for
      Cyclophilin A

<400> SEQUENCE: 4
tctgctgtct ttggaacttt gtctg                                        25

<210> SEQ ID NO 5
<211> LENGTH: 20
<212> TYPE: DNA
<213> ORGANISM: Artificial Sequence
<220> FEATURE:
<223> OTHER INFORMATION: synthetic construct; sense primer for
      activity-regulated gene

<400> SEQUENCE: 5
gtcccagatc cagaaccaca                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic construct; antisense primer for
      activity-regulated gene

<400> SEQUENCE: 6
cctcctcagc gtccacatac                                              20
```